United States Patent [19]

Kambara et al.

[11] Patent Number: 4,971,677
[45] Date of Patent: Nov. 20, 1990

[54] FLUORESCENCE DETECTION TYPE ELECTROPHORESIS APPARATUS

[75] Inventors: Hideki Kambara, Hachiouji; Yoshiko Katayama, Urawa; Tetsuo Nishikawa, Koganei, all of Japan

[73] Assignee: Hitachi, Ltd., Tokyo, Japan

[21] Appl. No.: 310,645

[22] Filed: Feb. 15, 1989

[30] Foreign Application Priority Data

Feb. 24, 1988 [JP]  Japan .................................. 63-39385

[51] Int. Cl.$^5$ ...................... B01D 57/02; G01N 27/26
[52] U.S. Cl. .............................. 204/299 R; 204/182.8; 356/344; 435/6
[58] Field of Search .......................... 204/299 R, 182.8; 356/344; 435/6

[56] References Cited

U.S. PATENT DOCUMENTS

| | | | |
|---|---|---|---|
| 4,123,343 | 10/1978 | Krupey et al. | 204/182.8 |
| 4,668,667 | 5/1987 | Moorehead et al. | 514/731 |
| 4,675,095 | 6/1987 | Kambara et al. | 204/299 R |
| 4,832,815 | 5/1989 | Kambara et al. | 204/299 R |
| 4,855,225 | 8/1989 | Fung et al. | 435/6 |

OTHER PUBLICATIONS

Ansorge et al., "A Non-Radioactive Automated Method for DNA Sequence Determination", Journal of Biochemical & Biophysical Methods, 13, (1986), 315–323.

Smith et al., "Fluorescence Detection in Automated DNA Sequence Analysis", Nature, 321, (Jun. 1986), 674–679.

Prober et al., "A System for Rapid DNA Sequencing with Fluorescent Chain-Terminating Dideoxynucleotides", Science, 238, (Oct. 1987), 336–341.

Primary Examiner—T. Tung
Assistant Examiner—David G. Ryser
Attorney, Agent, or Firm—Antonelli, Terry, Stout & Kraus

[57] ABSTRACT

In an electrophoresis apparatus for separating and detecting a sample of DNA or RNA labelled with fluorescence, use is made of a gel plate having a polyacrylamide concentration of 2 to 6% in order to greatly shorten the time required for the measurement.

6 Claims, 4 Drawing Sheets

FLUORESCENCE DETECTION TYPE ELECTROPHORESIS APPARATUS

BACKGROUND OF THE INVENTION

The present invention relates to an apparatus for determining base sequences of DNA or RNA. More specifically, the invention relates to a fluorescence detection type electrophoresis apparatus adapted for shortening the measuring time.

So far, base sequences of DNA's have been determined by labelling a DNA fragment with a radioactive element, transferring a pattern onto a photograph through autoradiography, the pattern being subjected to electrophoresis gel separation depending upon the length thereof, and reading the DNA band pattern, however, this method involves laborious work and time. A method, therefore, has been developed for determining the base sequence by separating and detecting DNA fragments in real time by using a fluorescence label instead of using a radioactive label. The real time detection method using a fluorescence label and the fluorescence detection type electrophoresis apparatus used for this method have been disclosed, for example, in "Journal of Biochemical and Biophysical Methods, 13, 1986, pp. 315–323", "Nature, Vol. 321, 1986, pp. 674–679", and "Science, Vol. 238, 1987, pp. 336–341".

According to the above prior art, however, a time which is as long as 5 to 10 hours is required from the start of migration of DNA fragments to the completion of measurement.

SUMMARY OF THE INVENTION

The object of the present invention is to provide a fluorescence detection type electrophoresis apparatus which is capable of carrying out the measurement within short periods of time overcoming difficulties involved in the above-mentioned prior art in determining the base sequences of DNA or RNA.

The above object of the present invention is achieved by optimizing various conditions in the electrophoresis gel migration. Concretely speaking, the object of the invention is achieved by selecting the polyacrylamide concentration of gel used for the electrophoresis separation device to be 2 to 6% (hereinafter, the polyacrylamide concentration is represented by the percentage of weight/volume (g/ml) of the total monomer concentration).

That is, the fluorescence detection type electrophoresis apparatus of the present invention comprises an electrophoresis separation device for electrophoresis-separating a sample labelled with fluorescence, an excitation light source for exciting the sample, and detection means for detecting the fluorescence emitted by the sample that is excited, in order to determine the base sequences of the sample, wherein use is made of a gel plate having 2 to 6% of a polyacrylamide concentration as the electrophoresis separation device.

Here, the electrophoresis separation device is one in which DNA or RNA fragments are allowed to undergo electrophoresis to effect electrophoresis separation depending upon the length of fragments, and includes at least, for example, an electrophoresis gel sandwiched between two transparent plates (quartz plate, etc.) and means for applying an electric field in the direction of migration.

According to the study by the present inventors, the reasons why the conventional fluorescence detection type electrophoresis apparatus requires a migration time of as long as 5 to 10 hours are that details of the electrophoresis gel migration phenomenon have not yet been clarified, that the real time detection method requires a long migration lane since the position resolution of fluorescence detection is poorer than the position resolution at the time of reading the band by visually observing the autoradiogram, and that in spite of this fact the measurement is taken using the electrophoresis separation device having an acrylamide concentration which is usually as high as about 8% just like in the autoradiography. The present was accomplished based upon the above-mentioned discovery by the present inventors.

Here, if a DNA fragment having a base length N migrates at a speed v(N), the time t required for migrating the migration lane of a length l is given by, $$t = l/v(N) \qquad (1)$$

The migration speed v(N) varies in proportion to the intensity of electric field E, and the proportional coefficient $v_0(N, C, T)$ is a function of the number of bases in the DNA fragment or the base length N, the polyacrylamide concentration C and the temperature T. Therefore, the equation (1) can be rewritten as, $$t = l/E \cdot v_0(N,C,T) \qquad (2)$$

The time t shortens with the increase in intensity of electric field resulting, however, in the generation of Joule's heat. Therefore, the temperature of the gel plate increases to make it difficult to separate the DNA band. Measurement can be taken within short periods of time if the DNA band is discriminated under the conditions of an electric field intensity and a temperature that do not hinder the measurement and if the gel concentration and the length l of migration lane are so selected that the time t is minimized.

The present invention employs the art of the conventional fluorescence detection type electrophoresis apparatus with the exception that the gel plate in the electrophoresis separation device has a polyacrylamide concentration of 2 to 6%.

DESCRIPTION OF THE PREFERRED EMBODIMENTS

An embodiment of the present invention will now be described in conjunction with FIGS. 1 to 5.

Figure 1:
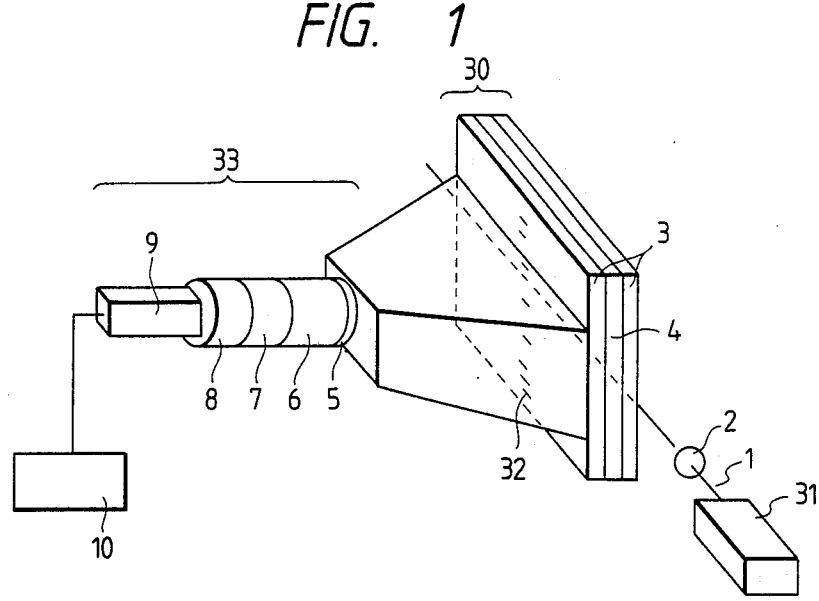
FIG. 1 is a schematic perspective view illustrating a fluorescence detection type electrophoresis apparatus according to an embodiment of the present invention.

FIG. 1 illustrates a fluorescence detection type electrophoresis apparatus according to the present invention. A laser beam 1 for excitation emitted from a laser source 31 passes through a lens 2 and enters into an electrophoresis gel 4 from the side surface thereof. The electrophoresis gel 4 is held by quartz plates 3. A sample 32 such as DNA labelled with fluorescence starts migration from the upper end of the gel 4 and proceeds toward the lower end of the gel 4 while undergoing electrophoresis separation. The laser beam 1 falls on a place separated by a predetermined distance away from a point where migration started, and the fluorescence from the fluorescence-labelled DNA that passes therethrough is collected by a lens 6 equipped with a filter 5, amplified through an image amplifier 7, permitted to pass through a relay lens 8, and is detected by a Vidicon camera 9 (trade name of RCA). The signals that are obtained are processed by a computer 10 and are output. The laser beam may be incident on the front surface while scanning over a predetermined lane instead of falling on the side surface. As will be understood from the equation (2), the migration time varies depending upon the distance l from the point where migration started to a portion irradiated with the laser beam, the concentration C of polyacrylamide, and the voltage V applied across the upper end and the lower end of the gel plate (or electric field intensity E in the gel).

The concentration of polyacrylamide of the gel plate can be easily learned from the amount of background fluorescence when irradiated with the laser beam or from the migration time of the DNA fragment.

Figure 4:
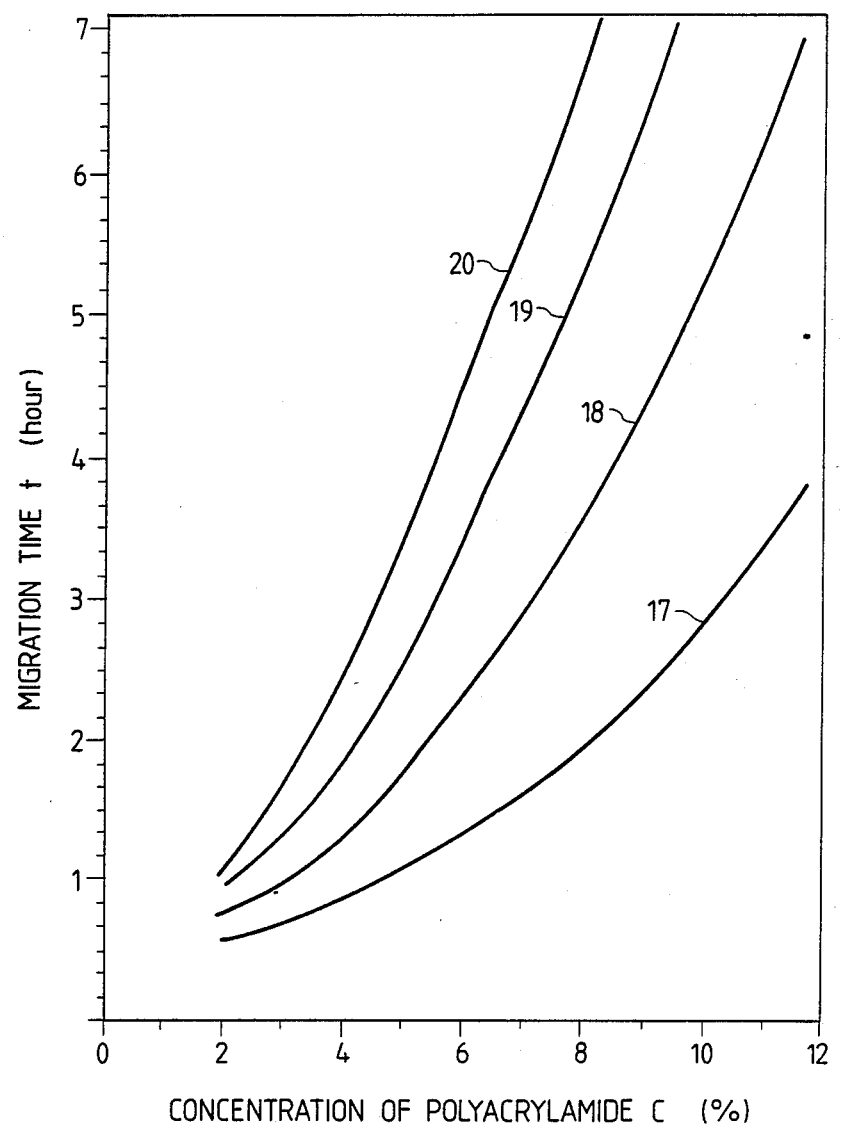
FIG. 4 is a graph showing relationships between the polyacrylamide concentration and the migration time of DNA fragments of various base lengths in the gel plates.

When the gel plate is maintained at a temperature of 48° C. and the electric field intensity is maintained at 50 V/cm, a time of about 85 minutes is required to migrate a DNA fragment of a 100 base length by 22 cm when the gel has a polyacrylamide concentration of 6%, and a longer period of time is required when the gel has a higher concentration. FIG. 4 shows relationships between the concentration of polyacrylamide in the gel and the migration time (details of FIG. 4 will be described later). The concentration of polyacrylamide of the gel can be learned from the migration time.

Background fluorescence when the gel plate is irradiated with the laser beam increases in proportion to the concentration of polyacrylamide. Therefore, the gel having a polyacrylamide concentration of, for example, 6% is prepared to measure the amount of background fluorescence and, then, a newly prepared gel is measured for its amount of background fluorescence and is compared with the case of 6%, so that the polyacrylamide concentration of the gel can be learned.

In FIG. 1, reference numeral 30 denotes an electrophoresis separation device (here, however, means for applying an electric field is a widely known one and is not diagrammed), and 33 denotes means for detecting fluorescence.

Figure 2:
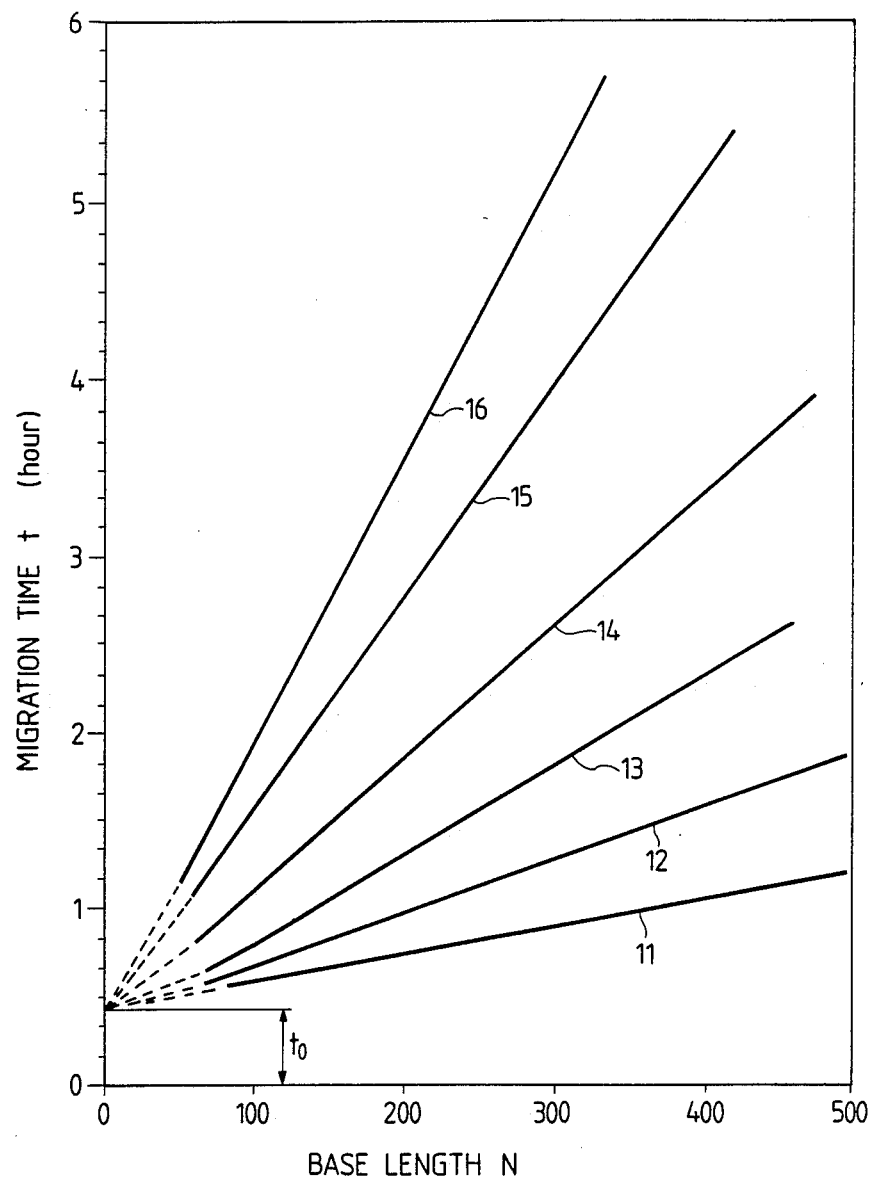
FIG. 2 is a graph illustrating relationships between the base length of a DNA fragment and the migration time in gel plates having various polyacrylamide concentrations.

FIG. 2 shows relationships between the base length (represented by the number of N of bases) of DNA fragments in the gels having various polyacrylamide concentrations and the migration time t. In FIG. 2, the curves 11, 12, 13, 14, 15 and 16 represent the cases where the gels have polyacrylamide concentrations of 2, 3, 4, 5, 6 and 8%. From the fact that the migration speed of the DNA fragment varies in proportion to the electric field intensity E and from the profiles of the curves of FIG. 2, the migration time t can be expressed as, $$t = \frac{l}{E}(f(C, T)N + g(T)) \quad (3)$$

where f(C, T) and g(T) are a function of the polyacrylamide concentration C and a function of the temperature T, and l denotes the length of the migration lane.

When the base length is approximated to zero, the migration time $t_0$ becomes equal to $l \cdot g(T)/E_0$ in the equation (3) irrespective of the concentration C.

From the equations (1) and (3), the migration speed v(N) of the DNA fragment can be expressed as, $$v(N) = \frac{E}{f(C, T)N + g(T)} \quad (4)$$

The interval d between the neighboring bands after the migration for a time t is given by, $$d = (v(N) - v(N+1)) t$$

$$= 1/(N + g(T)/f(C,T)) \quad (5)$$

It will be understood from this equation that when the base length N is great, the band interval d approaches 1/N without depending much upon the concentration C of polyacrylamide in the gel.

Figure 3:
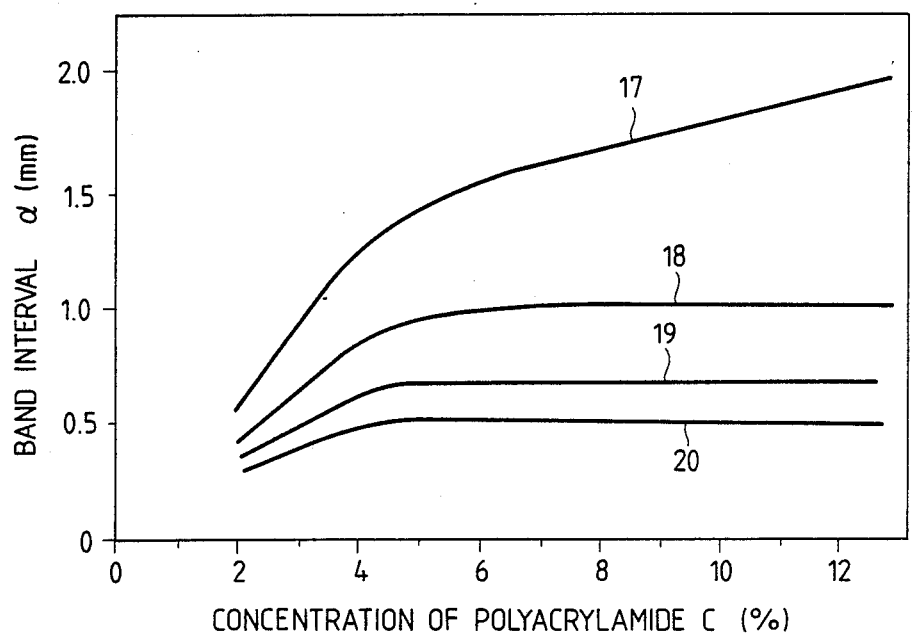
FIG. 3 is a graph showing relationships between the polyacrylamide concentration and the band interval of DNA fragments of various base lengths in the gel plates.

FIG. 3 shows practically measured dependency of the band interval upon the concentration for various base lengths. The migration distance is 22 cm. In FIG. 3, the curves 17, 18, 19 and 20 represent the cases where the DNA fragments have base lengths (represented by the number N of bases) of 100, 200, 300 and 400. When the base length is as short as about 100, the band interval d increases with increase in the gel concentration C. When the base length is 300 or 400, however, the band interval becomes nearly constant provided the gel concentration C is greater than 4%. On the other hand, it has been confirmed through experiment that the DNA band with width ω varies nearly in proportion to $\sqrt{l}$ almost without depending upon the gel concentration. The DNA band width ω therefore is given by, $$\omega = \omega_0(N, T)\sqrt{l} \quad (6)$$

where the proportional constant $\omega_0(N, T)$ is a function of the number N of bases and the temperature T.

FIG. 4 is a diagram showing the dependency of migration time of various base lengths upon the concentration of polyacrylamide in the gel, and wherein curves 17, 18, 19 and 20 represent the cases where the DNA fragments have base lengths (represented by the number N of bases of 100, 200, 300 and 400. It will be recognized from FIG. 4 that the migration time increases nearly in proportion to the square power of the concentration C. When the temperature is maintained constant, the migration time t is a function of the length l of migration lane and the gel concentration C. To discriminate the two neighboring bands, at least a relation d≧ω must hold true. Therefore, a gel concentration that makes the migration time t minimum is found with d=ω and letting the migration time t be a function of the gel concentration only.

From $d=\omega$ and the equation (6), the length l, i.e., $$l = \omega_0^2(N,T)(N+g(T)/f(C,T))^2 \qquad (7)$$

is found and is substituted for the equation (3) to obtain the following equation, $$t = \frac{\omega_0^2(N,\,T)\,(f(C,\,T)N + g(T))^3}{Ef^2(C,\,T)} \qquad (8)$$

From the equation (8), the value of C obtained as a solution of $dt/dC = 0$ stands for a gel concentration i.e., the value C that minimizes the migration time t stands for a gel concentration that is to be found.

From the following equation, $$\frac{dt}{dC} = \frac{\omega_0^2(N,\,T)}{E} \cdot \qquad (9)$$

$$\frac{3(f(C,\,T)N + g(T))^2 f(C,\,T)N - 2(f(C,\,T)N + g(T))^3}{f(C,\,T)^4} \times$$

$$f(C,\,T) \cdot \frac{df(C,\,T)}{dC} = 0$$

there is obtained $f(C,T)N = 2g(T)$.

That is, the gel concentrations C with which $$(t - t_0) = \frac{l}{E} f(C,\,T)N = \frac{l}{E} \cdot 2g(T) = 2 t_0$$

holds true on FIG. 4 make the migration time t minimum, the gel concentrations being 6.2%, 4.3%, 3.2% and 2.6% when the base lengths are 100, 200, 300 and 400. In the practical analysis, the base lengths in many cases lie from 200 to 300. In this case, the gel concentration C should be from 3.2 to 4.3%. In the case of FIG. 4, the migration time $t_0$ was 28 minutes. Therefore, the time t with which $t - t_0 = 2t_0$ holds is one hour and 24 minutes.

By substituting $f(C, T) = 2g(T)$ for the equation (7), the length l of gel migration necessary for the separation is found to be, $$l = \frac{9}{4} N^2 \omega_0^2(C,\,T) \qquad (10)$$

From the equation (6), $\omega_0(C, T)$ can be found using $\omega_{obs}/\sqrt{l}$ from the measured band interval $\omega_{obs}$ when the length of migration lane is $l_0$.

Table 1 shows polyacrylamide concentrations C that minimize the migration time required for discriminating the neighboring bands, the lengths l of migration lane and the migration times t when the gel plate has a thickness of 0.3 mm and the electric field of intensity is 50 V/cm for various base lengths.

TABLE 1

| Base length N | Concentration C of polyacrylamide | Length l of migration lane | Migration time t |
|---|---|---|---|
| 100 | 6.2% | 6 cm | 22 min. |
| 200 | 4.3% | 15 cm | 56 min. |
| 300 | 3.2% | 28 cm | 106 min. |
| 400 | 2.6% | 41 cm | 156 min. |

The values tabulated above are only rough indications that may undergo change to some extent depending upon the migration voltage, the temperature of the migration gel and the thickness of the gel. To realize the high-speed migration, however, it will be recognized that the concentration of polyacrylamide be 2 to 6%, which is much lower than that of the conventional art.

It will further be recognized that when the base lengths are 100 to 200, 200 to 300, and 300 to 400, the gel concentrations should preferably be 4.3 to 6.2, 3.2 to 4.3, and 2.6 to 3.2%.

Under the above-mentioned conditions, up to 300 bases can be measured in about 1.5 hours.

According to migration conditions corresponding to the base lengths shown in Table 1, it needs not be pointed out that DNA fragments having shorter base lengths can also be measured.

Figure 5:
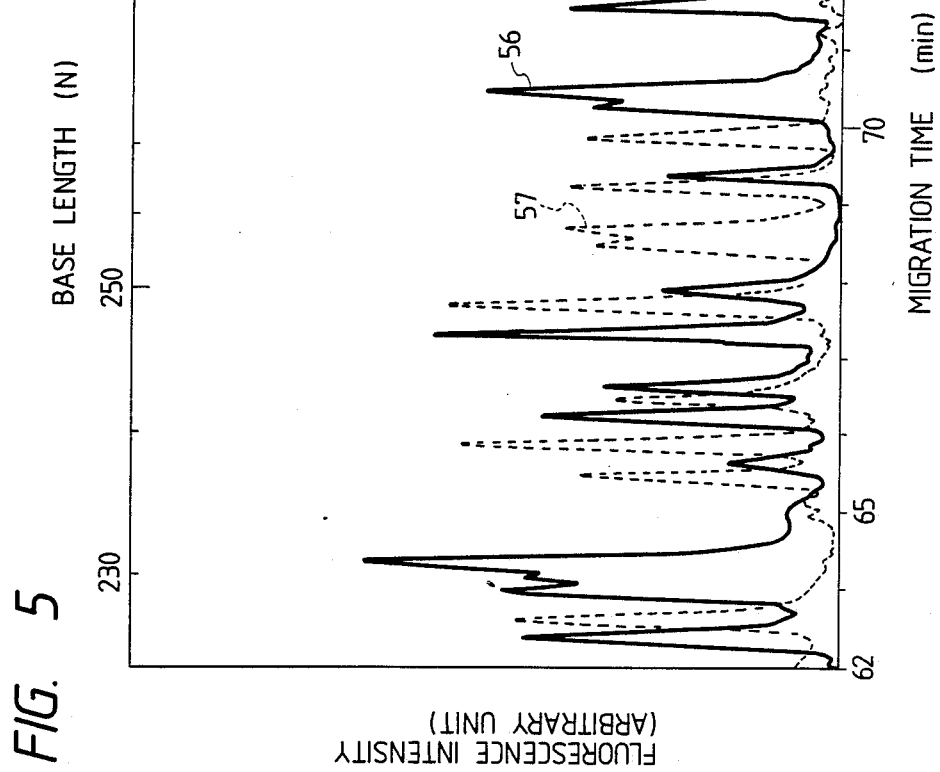
FIG. 5 is a graph showing spectra of DNA fragments when use is made of gel plate having a polyacrylamide concentration of 3% and a length of migration lane of 22 cm.

FIG. 5 shows the results of measurement using the gel having a polyacrylamide concentration of 3% and a migration lane of a length of 22 cm. The separation is not sufficient since the length of migration lane is shorter than 28 cm. It will, however, be comprehended that up to about 300 bases can be identified. The migration time of DNA fragment of a base length of 300 was 77 minutes.

In FIG. 5, the spectrum 56 is the one obtained from a DNA fragment group in which a base of nucleic acid at the terminal is guanine, and the spectrum 57 is the one obtained from a DNA group in which a base of nucleic acid at the terminal is thymine.

In this embodiment, the gels having various polyacrylamide concentrations were prepared in the same manner as in the prior art. Described below is a procedure for preparing a gel having a polyacrylamide concentration of 6%. Water is added to a mixture consisting of 1.14 g of an acrylamide monomer, 0.06 g of an N,N'-methylenebisacrylamide (the total amount with the acrylamide monomer is 1.2 g), 0.16 g of trishydroxyaminomethane, 0.08 g of boric acid, 0.014 g of EDTA·2Na and 6.3 g of urea, such that the total amount is 20 ml (i.e., the total amount of acrylamide monomer and N,N'-methylenebisacrylamide is 0.06 g in 1 ml). This is a polyacrylamide concentration of 0.06 g/ml which is expressed as 6%. Then, there are added 64 μl of ammonium persulfate of concentration of 15% and 10.7 μl of an N,N,N',N-tetramethylethylene diamine, and the mixture is left to stand at room temperature, whereby polymerization takes place to form a gel having a concentration of 6%.

According to the present invention as is obvious from the aforementioned embodiment, the DNA fragments that had hitherto been measured requiring a time of 5 to 10 hours can now be measured requiring a time of a little more than one hour. Thus, the measuring time required by the fluorescence detection type electrophoresis apparatus can be strikingly shortened.

In the fluorescence measuring system, furthermore, the light scattered by the gel and background fluorescence from impurities and/or gel imposes a lower limit for the detection. With the gel having a low concentration, however, the background fluorescence decreases, too, and the detection can be realized maintaining high sensitivity.

Though the aforementioned embodiment has dealt with the case of DNA, substantially the same results are obtained even in the case of RNA.

What is claimed is:

1. In a fluorescence detection type electrophoresis apparatus for determining base sequence of a sample in real time comprising an electrophoresis separation device for electrophoretically separating said sample labelled with fluorescence, an excitation light source for exciting said sample, and a detection means for detecting the fluorescence emitted by said sample that is excited, the improvement wherein use is made of a gel plate having a polyacrylamide concentration of 2 to 6% in terms of percentage of weight/volume (g/ml) of total monomer concentration as said electrophoresis separation device.

2. A fluorescence detection type electrophoresis apparatus according to claim 1, wherein said polyacrylamide concentration is from 3.2 to 4.3%.

3. A fluorescence detection type electrophoresis apparatus according to claim 1, wherein said polyacrylamide concentration is from 2.6 to 3.2%.

4. In a fluorescence detection type electrophoresis apparatus for determining base sequence of a sample of DNA or RNA in real time comprising an electrophoresis separation device for electrophoretically separating said sample labelled with fluorescence, an excitation light source for exciting said sample, and a detection means for detecting the fluorescence emitted by said sample that is excited, the improvement wherein use is made of a gel plate having a polyacrylamide concentration of 2 to 6% in terms of percentage of weight/volume (g/ml) of total monomer concentration as said electrophoresis separation device.

5. A fluorescence detection type electrophoresis apparatus for determining base sequence of a sample of DNA or RNA labelled with fluorescence in real time comprising:

an electrophoresis separation device comprising a gel plate holding an electrophoresis gel for electrophoretically separating said sample by migration of said sample from a first end of said gel towards a second end of said gel, wherein said gel contains polyacrylamide at a concentration of 2 to 6% in terms of percentage of weight/volume (g/ml) of total monomer concentration;

an excitation light source directed on said gel at a position separated by a predetermined distance from said first end for exciting said sample; and a detection means for detecting fluorescence emitted by said sample as it is excited and passes through said position;

whereby said base sequence of said sample can be determined by separating and detecting fragments of said sample in real time.

6. A fluorescence detection type electrophoresis apparatus for determining base sequence of a sample in real time comprising an electrophoresis separation device for electrophoretically separating said sample labelled with fluorescence, and excitation light source for exciting said sample, and a detection means for detecting the fluorescence emitted by said sample that is excited, the improvement wherein use is made of a gel plate having a polyacrylamide concentration of from 4.3 to 6.2% in terms of percentage of weight/volume (g/ml) of total monomer concentration as said electrophoresis separation device.

* * * * *